United States Patent [19]

Abdul-Malak et al.

[11] Patent Number: 5,567,806

[45] Date of Patent: Oct. 22, 1996

[54] COLLAGEN CROSSLINKED WITH A CROSSLINKING AGENT FOR THE MANUFACTURE OF A SUTURABLE, BIOCOMPATIBLE SLOWRESORBING MEMBRANE, AND SUCH A MEMBRANE

[76] Inventors: Nabil Abdul-Malak, 27, rue Frederic Mistral, 69300 Caluire; Jean Fourcart, Place de l'Orme Baslieux les Fismes, 51170 Fismes; Alain Huc, 26, chemin des Santons, 69110 Ste Foy les Lyon, all of France

[21] Appl. No.: 469,790

[22] Filed: Jun. 6, 1995

Related U.S. Application Data

[63] Continuation of Ser. No. 185,917, filed as PCT/FR92/00750 Jul. 30, 1992, abandoned.

[30] Foreign Application Priority Data

Aug. 2, 1991 [FR] France .................... 91 09909

[51] Int. Cl.⁶ .................... A61K 35/32; A61K 38/39; C07K 14/78; A61L 15/20
[52] U.S. Cl. .................... 530/356; 530/840; 530/842; 424/444; 602/50; 602/900; 128/DIG. 8
[58] Field of Search .................... 530/356, 840, 530/842; 514/12, 21, 801; 424/443, 444, 445, 447, 449, 484; 602/42, 43, 44, 45, 48, 50, 900; 106/124; 128/DIG. 8

[56] References Cited

U.S. PATENT DOCUMENTS

| | | | |
|---|---|---|---|
| 4,280,954 | 7/1981 | Yannas et al. | 530/356 |
| 4,670,014 | 6/1987 | Huc et al. | 424/94.1 |
| 4,980,403 | 12/1990 | Bateman et al. | 524/17 |
| 5,206,028 | 4/1993 | Li | 424/484 |
| 5,264,551 | 11/1993 | Petite et al. | 530/356 |

FOREIGN PATENT DOCUMENTS

| | | |
|---|---|---|
| 0052288 | 5/1982 | European Pat. Off. . |
| 0156740 | 10/1985 | European Pat. Off. . |
| 0187014 | 7/1986 | European Pat. Off. . |
| 0331786 | 9/1989 | European Pat. Off. . |
| WO9012055 | 10/1990 | WIPO . |
| WO9013302 | 11/1990 | WIPO . |

*Primary Examiner*—Mindy Fleisher
*Assistant Examiner*—Nancy J. Degen
*Attorney, Agent, or Firm*—Wolf, Greenfield & Sacks, P.C.

[57] ABSTRACT

Suturable, biocompatible, control-resorbing membranes are disclosed for use in guided tissue regeneration, comprising a cross-linked collagen material either obtained by crosslinking a starting collagen material in the coagulated state produced by coagulation of a collagen material gel with a coagulating agent or obtained by crosslinking of a sponge of a collagen material on which a collagen material gel has been poured before performing the crosslinking.

31 Claims, No Drawings

COLLAGEN CROSSLINKED WITH A CROSSLINKING AGENT FOR THE MANUFACTURE OF A SUTURABLE, BIOCOMPATIBLE SLOWRESORBING MEMBRANE, AND SUCH A MEMBRANE

This application is a continuation of application Ser,. No. 08/185,917, filed as PCT/FR92/00750 Jul. 30. 1992, entitled UTILIZATION OF CROSSLINKED COLLAGEN FOR THE FABRICATION OF A STITCHABLE BIOCOMPATIBLE SLOW RESORPTION MEMBRANE, now abandoned.

The invention relates to essentially to the use of collagen crosslinked with a crosslinking agent for the manufacture of a suturable, bicompatible slow-resobing membrane, and to such membrane. Such a membrane can advantageously be used for a guided tissue regeneration.

The concept of guided tissue regeneration was recently developed by Nieman and in practice involves the use of a biocompatible material capable of separating two cell populations in vivo.

The principle is as follows:

When an empty space is created in a living tissue, it is filled by the most rapidly multiplying cell line adjacent to this void, unless access is deliberately limited to a single cell type, which will then be the only one colonize the void to be filled.

The principle is utilized in guide tissue regeneration for directing the repair of damage tissues in the manner desired by the clinician.

Thus, for example, in the case of periodontology, it is very difficult to repair damaged periradicular ligamentaous tissue. In fact, during the periodontum healing process, the epithelium regenerates more rapidly than the ligament and tends to take its place.

The guided tissue regeneration technique used in this case consists insolating the region normally occupied by the ligament, so as make it inaccessible to the epitheium. This operation can be performed with a bicompatible material implanted in the tissues. The object of the present invention is to described such a material.

Two types of product are currently known to be used for the purpose of this guided tissue regeneration.

Firstly, the expanded polytetrafluoroethylene membranes marketed under the trademark Gore-Tex® are known, which are not resorbable. These have the advantage of remaining intact throughout the time for which they are implanted, and thereby perfectly fulfil the barrier function they have to perform.

However, they cannot be left in place indefinitely and require two surgical interventions, namely one to insert the material and a second, six to eight weeks later, to remove it once the regeneration phenomenon has been initiated.

On the other hand, resorbable membranes, composed of collagen or other polymers such as polyglycolates, do not require an intervention for removal since they are eliminated by resorption.

Their resorption time is relatively short, however, and they do not always remain intact for long enough to initiate sufficient regeneration.

One object of the present invention is therefore to provide a novel membrane material for guided tissue regeneration which is suturable, biocompatible and slow-resorbing.

A further object of the present invention is to provide a special process for the manufacture of the base material of such membranes.

The present invention makes it possible for the first time to solve this technical problem in a simple, reliable and inexpensive manner which can be used on the industrial and medical scale.

Thus, according to a first feature, the present invention provides a use of collagen crosslinked with a crosslinking agent for the manufacture of a suturable, biocompatible slow-resorbing membrane for guided tissue regeneration.

In one variant, the starting collagen is in the coagulated state produced by coagulating a collagen gel with a coagulating agent.

In one variant, the degree of crosslinking is such as to increase the denaturation temperature of the collagen by at least 15° C., preferably at least 20° C., compared with native collagen.

The crosslinking agent can be selected from any of the known collagen crosslinking agents. For example, it can be an aldehyde such as a dialdehyde, in particular glutaraldehyde. Preferably, however, the crosslinking agent consists of diphenylphosphoryl azide (abbreviated to DPPA). In contrast to most of the other crosslinking agents, DPPA induces crosslinking and does not bind to the material.

The crosslinking process itself is well known to those skilled in the art. For a DPPA crosslinking process, reference may be made to an earlier patent application in the name of the Applicant, published under no. FR-A-2 645 870, which is incorporated here by way of reference.

The collagen used can be native collagen, in particular of type I or type III.

In one particular variant; it is also possible to use atelocollagen, although this is less preferable.

In another particular embodiment, a mixture of collagen or atelocollagen and glycosaminoglycans is used, this mixture being crosslinked with the cross-linking agent.

In one particularly advantageous variant of the use according to the invention, it is possible to manufacture a mixed membrane comprising a crosslinked layer of collagen and a layer of collagen or atelocollagen/glycosaminoglycan mixture, these two layers being crosslinked with the above-mentioned crosslinking agent.

In another advantageous variant, the above-mentioned membrane is made porous to have a sponge-like appearance, having been prepared by a step involving the lyophilization of a starting gel.

According to a second feature, the present invention also covers a suturable, biocompatible slow-resorbing membrane comprising collagen, for guided tissue regeneration, said membrane comprising collagen crosslinked with a crosslinking agent.

In one variant, the degree of crosslinking is such as to increase the denaturation temperature of the crosslinked collagen by at least 15° C., preferably at least 20° C., compared with native collagen. The preferred crosslinking agent is diphenylphosphoryl azide, abbreviated to DPPA.

In one advantageous variant, the collagen is a native collagen of type I or type III.

In another variant, the collagen is atelocollagen.

In another variant, the collagen or atelocollagen is mixed with a glycosaminoglycan before the whole is crosslinked with the above-mentioned crosslinking agent.

In another particular variant of the membrane, the latter is porous, having been prepared in particular by a step involving the lyophilization of a starting gel.

In another variant, this membrane comprises at least two layers, namely a first layer of crosslinked collagen and a second layer of a collagen or atelocollagen/glycosaminoglycan mixture.

Glycosaminoglycans which can advantageously be used within the framework of the present invention are a structural glycosaminoglycan, in particular hyaluronic acid, chondroitin 4-sulfate, chondroitin 6-sulfate, dermatan sulfate, heparan sulfate, keratan sulfate and heparin and its derivatives, in particular heparins with a low molecular weight of between about 2000 and about 10,000.

The proportion of glycosaminoglycans relative to the collagen or atelocollagen is preferably between 18 and 25%.

The glycosaminoglycan and the collagen or atelocollagen are mixed in solution form. For example, the glycosaminoglycan is in the form of an aqueous solution of glycosaminoglycans containing from 0.5 to 4% by weight, more particularly from 0.5 to 2% by weight and preferably about 1% of glycosaminoglycans. Likewise, the collagen or atelocollagen can be in the form of an aqueous solution having a concentration of between 0.5 and 2% by weight, preferably about 1% by weight, of collagen or atelocollagen. The solution of collagen or atelocollagen can be prepared according to the invention by dissolving collagen or atelocollagen fibers in a slightly acidic aqueous solution, in particular a 0.1M aqueous solution of acetic acid.

Provision can be made to bring the mixture of collagen or atelocollagen and glycosaminoglycans to a pH close to neutrality and in particular to a pH of between 6.5 and 8. An aqueous solution of sodium hydroxide can be used for this purpose.

According to a third feature, the present invention relates to a specific process for the preparation of the starting collagen. This process is independently patentable and constitutes an independent invention.

This process comprises the preparation of a collagen wherein this gel is coagulated with a coagulating agent comprising an ammoniacal solution preferably having a dehydrating effect.

In one advantageous embodiment of this coagulation process, the ammoniacal solution is an organic ammoniacal solution using acetone as the dehydrating agent. In fact, a synergistic effect is observed with the combination acetone/aqueous ammonia for coagulating the gel and removing the water present in the gel.

The ratio acetone/aqueous ammonia is preferably between 50/50 and 80/20 by volume and particularly preferably 70/30 by volume.

In one advantageous variant, when the amounts of gel to be coagulated are relatively large, the coagulating solution is renewed during coagulation.

In one particular variant, the gel is run through a die of appropriate shape and cross-section to produce a coagulated gel in the appropriate form. If the cross-section of the die is rectangular, a film is obtained; this will subsequently form the membrane.

The coagulated gel obtained can then be cross-linked with the above-mentioned crosslinking agent.

Other variants of the process are also possible in the context of the foregoing features of the invention. In particular, the collagen can be native collagen, especially of type I or type III, or else it can in practice be atelocollagen, i.e. collagen from which the telopeptides have been removed. Moreover, the collagen can be mixed with a glycosaminoglycan.

Thus it is seen that the invention affords all the decisive technical advantages referred to above, as well as the technical advantages which will become apparent to those skilled in the art on the basis of the following explanatory description of the invention referring to two currently preferred embodiments of the invention, which are given simply by way of illustration and cannot therefore in any way limit the scope of the invention. The percentages are given by weight in the Examples, unless indicated otherwise.

EXAMPLE 1

Preparation of a crosslinked simple collagen membrane

A—Extraction of the native collagen and preparation of the gel:

A gel is prepared from calf skins which have first been washed and depilated with a lime/sulfide mixture (lime: 4%, sodium sulfide: 3%).

It is then unlimed in a bath containing ammonium chloride (2%) and sodium metabisulfite (0.5%). It is then neutralized, after which the salts are removed by two washes with water. It is subsequently ground and then washed with phosphate buffer of pH 7.8 (potassium dihydrogen phosphate 0.78 g/l and disodium monohydrogen phosphate 21.7 g/l). The phosphate is then removed by two successive washes with softened water.

The ground material is then acidified with a 10% solution of acetic acid, the amount of acetic acid being 5% relative to the collagen. The ground material is then malaxated to give a homogeneous paste. This paste is then diluted to give a gel having a concentration of 0.75% of native collagen.

B—Preparation of the film

The gel obtained is degassed under vacuum and then run into a coagulating bath through a rectangular die whose cross-section has a height of 0.5 mm. The coagulating solution is an acetone/aqueous ammonia mixture (70/30 v/v), which is renewed for every 250 ml of gel.

The film obtained is then dried in air at room temperature on a plastic polytetrafluoroethylene support. When dry, the film is easily detached from its support.

C—Crosslinking of the film

The film is then placed for 24 h at 4° C. in a solution of dimethylformamide (DMF) containing 0.5% of diphenylphosphoryl azide (DPPA), the concentration being expressed by volume. The DPPA is removed from the membrane by rinsing in a borate buffer solution of pH 8.9 (sodium tetraborate 0.04M, boric acid 0.04M).

The membrane is subsequently incubated for 15 h in the borate buffer solution of pH 8.9 and then rinsed 5 times with deionized water before being placed in a 10% solution of glycerol.

It is then dried in air and sterilized with γ radiation at a dose of 25 kGy (kilogray). The initial and final temperatures of denaturation of the collagen of this membrane are 64° and 80° C. respectively.

EXAMPLE 2

Preparation of a mixed membrane of crosslinked collagen/glycosaminoglycan

A—Extraction of the native collagen and preparation of the gel

A gel is prepared from calf skins which have first been washed and depilated with a lime/sulfide mixture (lime: 4%, sodium sulfide: 3%).

It is then unlimed in a bath containing ammonium chloride (2%) and sodium metabisulfite (0.5%). It is then neutralizedr after which the salts are removed by two washes with water. It is subsequently ground and then washed with phosphate buffer of pH 7.8 (potassium dihydrogen phosphate 0.78 g/l and disodium monohydrogen phosphate 21.7 g/l). The phosphate is then removed by two successive washes with softened water.

The ground material is then acidified with a 10% solution of acetic acid, the amount of acetic acid being 5% relative to the collagen. The ground material is then malaxated to give a homogeneous paste. This paste is then diluted to give a gel having a concentration of 0.75% of native collagen.

B—Preparation of the chondroitin 4-sulfate

Lambs' nasal septa from which the muscular and adipose tissues have been removed are chopped and ground by extrusion through a grid having 4 mm holes; the ground material is placed for 24 h at a temperature of 6° C. in a potassium chloride buffer (KCl 11.8 g/l, cysteine 78.8 mg/l, EDTA 180 mg/l) containing 1% of "MERCK" papain, the proportion being 130 g of ground material per 1 of buffer.

The supernatant is separated from the residue by continuous centrifugation in a centrifuge rotating at 4000 rpm. 40 g/l of trichloroacetic acid are then added to the supernatant. The precipitate is removed by continuous centrifugation according to the above technique. The supernatant is neutralized with sodium hydroxide pellets. The mixture is then dialyzed against sterile deionized water using gut with a cutoff threshold of between 6000 and 8000 daltons. The dialyzed solution is lyophilized. The chondroitin 4sulfate is obtained in the dry state.

C—Preparation of the collagen/chondroitin 4-sulfate sponge 1.87 g of chondroitin 4-sulfate are added to 1l of 0.75% collagen gel. After neutralization, the mixture is stirred and then lyophilized. The sponge obtained is compressed for 15 s under a pressure of 150 bar.

D—Preparation of the mixed membrane

The 1% collagen gel is run onto the compressed sponge through a die whose cross-section has a height of 0.3 cm. 10 ml of gel are deposited on 35 cm$^2$ of sponge. The resulting membrane is dried in the open air.

E—Chemical crosslinking of the membrane

The dried membrane is incubated for 24 h at 4° C. in a solution of DMF containing 0.5% of DPPA, the concentration being expressed by volume. The DPPA is removed from the membrane by rinsing in a borate buffer solution of pH 8.9 (sodium tetraborate 0.04M, boric acid 0.04M). The membrane is subsequently incubated for 15 h in the borate buffer solution of pH 8.9 and then rinsed 5 times with deionized water before being placed in a 10% aqueous solution of glycerol.

The membrane is then dried in air and sterilized with 7 radiation at a dose of 25 kGy (kilogray). The initial and final temperatures of denaturation of the collagen of this membrane are 60° and 85° C. respectively.

The membranes according to the invention can be used as a material for guided tissue regeneration, preferably in dental surgery, for example for filling periodontal pockets, raising maxillo-mandibular ridges or regenerating bone around an implant.

Periodontal pockets are deepenings of the gingival sulcus resulting from bacterial attack of the tissues supporting the tooth.

They are characterized by a loss of the bone substance which is normally present around the root of the tooth and which serves to support it on the jaw.

To use the coilagen membrane in this case, the practitioner creates a full thickness flap to expose the damaged bone. He applies the membrane to the bone so as to cover the damage completely and overlap the crown slightly. He finally closes the flap by suturing it so as to leave the membrane overlapping very slightly in the sulcus.

The intervention can also be performed with the concomitant use of biomaterials and bone filling. This technique makes it possible to repair the damaged tissues in 4 to 8 months.

The removal of a tooth from a buccal region is often accompanied by large losses of bone. The surgeon can make good these losses by applying the membrane to the bone so as to cover and overlap the lost bone, taking care to ensure that the space to be reconstructed between the membrane and the bone has the desired shape for reconstruction and, if necessary, that this shape is maintained by using, underneath the membrane, a material which is compatible with the new bone growth. Finally, he carefully closes the flap to achieve reconstruction in 4 to 8 months.

The surgical implantation of biocompatible artificial metal roots or dental implants in the bone of toothless jaws is a widely used technique in dental surgery.

It often happens that these implants are inserted under conditions which do not allow them to be in contact with the bone over their entire radicular surface, said bone being missing at certain points.

Once again, the use of collagen membranes will enable the surgeon to repair the damaged bone contiguous to the implant.

In this case he will simply use a membrane to cover the region of bone where the implant is inserted, before closing the flap created at the start of the intervention, to give perfect integration of the implant with the bone in 3 to 6 months.

The present invention covers all the means which consist of technical equivalents of the means described and the various combinations thereof.

Furthermore, the invention covers any characteristic which appears to be novel in relation to any state of the art and which results from the foregoing description taken as a whole.

What is claimed is:

1. A process of manufacture of a suturable, biocompatible, controlled-resorbing, mixed membrane, comprising the following steps:

a) preparing a sponge of a mixture of a collagen material and of a glycosaminoglycan;

b) compressing said sponge under a pressure of about 150 bars;

c) pouring a collage gel onto said sponge; and d) cross-linking said sponge with said collagen gel, with a cross-linking agent.

2. The process of claim 1, wherein said cross-linking agent is diphenylphosphoryl azide.

3. The process of claim 1, wherein said sponge is prepared from is mixture of native collagen with a glycosaminoglycan.

4. The process of claim 3, wherein said glycosaminoglycan is selected from the group consisting of chondroitin 4-sulfate, chondritin 6-sulfate, dermatan-sulfate, heparan sulfate, keratan sulfate and hyaluronic acid.

5. The process of claim 1, wherein said membrane is a membrane for guided tissue regeneration.

6. A suitable, bicompatible, controlled-resorbing membrane comprising a collagen material cross-linked with a cross-linking agent, wherein said cross-linked collagen material is obtained by cross-linking of a sponge of a collagen material which has been compressed under a pressure of about 150 bars and on which compressed sponge a collagen material gel has been poured before performing said cross-linking.

7. The membrane of claim 6, wherein said collagen material is selected from the group consisting of native collagen and atelocollagen.

8. The membrane of claim 6, wherein said sponge includes a mixture of an atelocollagen and glycosaminoglycan.

9. The membrane of claim 8, wherein said glycosaminoglycan is selected from the group consisting of chondroitin 4-sulfate, chondroitin 6-sulfate, dermatan sulfate, heparan sulfate, keratan sulfate and hyaluronic acid.

10. The membrane of claim 6, wherein said cross-linking provides a degree of cross-linking increasing the denaturation temperature of the cross-linked collagen material by at least 15° C., as compared with native collagen.

11. The membrane of claim 10, wherein said cross-linking provides a degree of cross-linking increasing the denaturation temperature of cross-linked collagen material by at least 20° C., as compared with native collagen.

12. The membrane of claim 6, wherein the cross-linking agent is diphenylphosphoryl azide.

13. The membrane of claim 6, wherein said membrane is a membrane for guided tissue regeneration.

14. A process for guided tissue regeneration, comprising using a cross-linked collagen material as obtained by cross-linking a sponge of collagen material which has been compressed under a pressure of about 150 bars and on which compressed sponge, a collagen material gel has been poured before performing said cross-linking.

15. The process of claim 14, wherein the collagen material is native collagen selected from the group consisting of collagen of type I and collagen of type III.

16. The process of claim 14, wherein the collagen material is atelocollagen.

17. The process of claim 14, wherein said cross-lining provides a degree of cross-linking increasing the denaturation temperature of the cross-linked collagen material by at least 15° C. as compared with native collagen.

18. The process of claim 14, wherein said cross-linking provides a degree of cross-linking increasing the denaturation temperature of the cross-linked collagen material by at least 20° C. as compared with native collagen.

19. The process of claim 14, wherein said cross-linking is performed with diphenylphosphoryl azide and provides a degree of cross-linking increasing the denaturation temperature of the cross-linked collagen material by at least 15° C. as compared with native collagen.

20. The process of claim 14, wherein said sponge is produced from a mixture of native collagen and a glycosaminoglycan.

21. The process of claim 20, wherien said glycosaminoglycan is selected from the group consisting of chondrotion 4-sulfate, chondrotin 6-sulfate, dermatan sulfate, heparan sulfate, keratan sulfate and hyaluronic acid.

22. The process of claim 14, wherein after cross-linking, a drying is performed in air.

23. The process of claim 14, wherein said cross-linked collagen material has a temperature of denaturation of the collagen ranging between about 80° and 85° C.

24. The process of claim 23, wherein said collagen material is native collagen, and said collagen material further comprises a glycosaminoglycan.

25. The process of claim 14, wherein said sponge is produced from a mixture of native collagen and of a glycosaminoglycan which is substantially neutralized, said glycosamionoglycan being selected from the group consisting of chondroitin 4-sulfate, chondroitin 6-sulfate, dermatan sulfate, heparan sulfate, keratan sulfate and hyaluronic acid.

26. A process for guided tissue regeneration using a cross-linked collagen material, comprising:

a) preparing a sponge of a collagen material;

b) compressing the collagen material under a pressure of about 150 bars; and c) cross-linking the compressed sponge of collagen material.

27. The process of claim 26, wherein the collagen material is a native collagen and is selected from the group consisting of a collagen of type I and a collagen of type III.

28. The process of claim 26, wherein the collagen material is a mixture of a native collagen and a glycosaminoglycan.

29. The process of claim 26, wherein the step of cross-linking increases a denuturation temperature of the cross-linked collagen material by at least 15° C. over that of a native collagen, and wherein step (c) includes a step of:

drying the cross-linked collagen sponge of collagen material in air.

30. A process for guided tissue regeneration using a cross-linked collagen material, comprising:

(a) preparing a sponge of a collagen material;

(b) compressing the sponge of collagen material under pressure of at least about 150 bars;

(c) cross-linking the sponge of collagen material to provide a denaturation temperature of the cross-linked collagen material which is at least 15° C. greater than a denuaturation temperature of a native collagen; and (d) drying the cross-linked sponge of collagen material in air.

31. The process of claim 30, further comprising pouring a collagen material gel on the sponge of collagen material prior to performing the cross-linking step.

* * * * *